United States Patent [19]

Kolar et al.

[11] Patent Number: 5,556,941
[45] Date of Patent: Sep. 17, 1996

[54] GLYCOPEPTIDE DERIVATIVES, A PROCESS FOR THEIR PREPARATION AND PHARMACEUTICAL AGENTS CONTAINING THESE COMPOUNDS

[75] Inventors: Cenek Kolar, Marburg; Werner Stüber, Lahntal, both of Germany

[73] Assignee: Behringwerke Aktiengesellschaft, Marburg, Germany

[21] Appl. No.: 291,729

[22] Filed: Aug. 16, 1994

Related U.S. Application Data

[63] Continuation of Ser. No. 25,798, Mar. 3, 1993, abandoned.

[30] Foreign Application Priority Data

Mar. 5, 1992 [DE] Germany .......................... 42 06 858.4

[51] Int. Cl.$^6$ .......................... A61K 38/14; C07K 5/072; C07K 9/00
[52] U.S. Cl. .......................... 530/322; 514/8; 536/29.11
[58] Field of Search .......................... 530/322; 514/8, 514/19; 536/17.6, 19.11, 29.13

[56] References Cited

U.S. PATENT DOCUMENTS

| | | | |
|---|---|---|---|
| 4,791,102 | 12/1988 | Bernat et al. | 514/19 |
| 4,977,168 | 12/1990 | Bernat et al. | 514/330 |
| 5,218,092 | 6/1993 | Sasaki et al. | 530/351 |

FOREIGN PATENT DOCUMENTS

| | | | |
|---|---|---|---|
| 0513543A1 | 11/1992 | European Pat. Off. | C07K 5/06 |
| WO88/02756 | 4/1988 | WIPO . | |

OTHER PUBLICATIONS

"The Peptides", Geiger et al., Academic Press, 3:24 (1981).
"Synthesis Of Glycosylamides and 4–N–Glycosyl–L–Asparagine Derivatives", Khorlin et al., Carbohydrate Research, 85:201–208 (1980).
"The synthesis and structure of some N–(L–aspart–4–oyl)–β–D–xylopyranosylamine derivatives", Walczyna et al., Carbohydrate Research, 180:147–151 (1988).
"Eine Einfache Synthese Von N–Acyl–Glykoslaminen", Klemer et al., J. Carbohydrate Chemistry, 7(4):785–797 (1988).
"Synthesis of the α and β anomer of an N–triglycosyl dipeptide", Takeda et al., Carbohydrate Research, 207:71–79 (1990).
"Synthese eines β–Mannosyl–Chitobiosyl–Asparagin–Konjugates—eines zentralen Elements der Core–Region von N–Glycoproteinen", Guenther et al., Angew. Chem., 102(9):1068 (1990).
"Solid–Phase Synthesis of Glycopeptides: Synthesis of $N^\alpha$–Fluorenylemeth–Oxycarbonyl L–Asparagine $N^\beta$–Glycosides", Urge et al., Tetrahedron Letters, 32(29):3445–3448 (1991).
"Synthesis of glycosylated tuftsins and tuftsin–containing IgG fragment undecapeptide", Biondi et al., Int. J. Peptide Protein Res., 37:112–121 (1991).

Kaiser et al., "Pharmacological characterization of a new highly effective synthetic thrombin inhibitor," *Biomed. Biochim. Act9*, 44, 1201–1210 (1985).
J. Hauptmann et al., *Thrombosis and Haeomostasis*, vol. 63(2), pp. 220–223 (1990).
B. Kaiser et al., *Biomed. Biochim. Acta*, vol. 44, pp. 120–1210 (1985).
R. Kikumoto et al., *Biochemistry*, vol. 23, pp. 85–90 (1984).

*Primary Examiner*—Jeffrey E. Russel
*Attorney, Agent, or Firm*—Finnegan, Henderson, Farabow, Garrett & Dunner, L.L.P.

[57] ABSTRACT

Glycopeptide derivatives, a process for their preparation and pharmaceutical agents containing these compounds N-Glycopeptide derivatives of the formula I

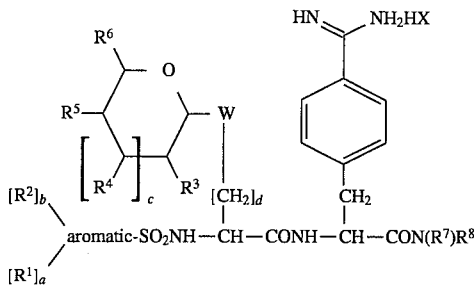

where
aromatic is an unsubstituted or substituted benzene residue, naphthalene residue, chroman residue, chromene residue or coumarone residue, a is 0 to 5, b is 0 to 4, c is 0 or 1, d is 1 or 2

$R^1$ is $(C_1-C_3)$-alkyl, $R^2$ is $(C_1-C_3)$-alkyl or $(C_1-C_3)$-alkyloxy, $R^3$ is H, OH, $(C_1-C_3)$-alkyloxy, $NH_2$, $NH-(C_1-C_6)$-alkanoyl, NH-benzoyl, $NH-SO_3H$ or NH-acyl radical of a natural N-acetylated amino acid, $R^4$ is H, OH, or $(C_1-C_3)$-alkyloxy, $R^5$ is H, OH, $(C_1-C_3)$-alkyloxy, fluorine, chlorine or bromine, $R^6$ is H, $CH_3$, $CH_2OH$, $CH_2O-(C_1-C_6)$, $CH_2NHCOCH_3$ or $CH_2NH-SO_3H$, $R^5$ and $R^6$ are together $O-CH_2-O-CH_2$, $-O-CH(CH_3)-O-CH_2$ or $O-C(CH_3)_2-O-CH_2$, $R^7$ is hydroxy-$(C_2-C_4)$-alkyl or $(C_2-C_4)$-alkyloxy-$(C_2-C_4)$-alkyl, $R^8$ is H or $(C_1-C_6)$-alkyl or $R^7$-N-$R^8$ are together a pyrrolidine ring or piperdine ring or morpholine ring, which can be substituted by HO, $HOCH_2$, $CH_3$ or COOH, W is $-O-$, $-CONH-$ or $-C_6H_4-CONH$ and H-X is HCl, a $(C_1-C_7)$-alkanoic acid or another pharmacologically tolerated inorganic or organic acid, are described, as are a process for their preparation and a pharmaceutical agent which contains these novel compounds. These pharmaceuticals can be used in particular for the therapy of thrombotic disorders.

4 Claims, No Drawings

GLYCOPEPTIDE DERIVATIVES, A PROCESS FOR THEIR PREPARATION AND PHARMACEUTICAL AGENTS CONTAINING THESE COMPOUNDS

This application is a continuation of application Ser. No. 08/025,798, filed Mar. 3, 1993, now abandoned.

The invention relates to N-glycopeptide derivatives, a process for their preparation and a pharmaceutical agent which contains these novel compounds.

The main step in the coagulation of blood involves the conversion of the soluble protein fibrinogen into the insoluble protein fibrin. For this, a proteolytic catalyst, thrombin, is necessary. By proteolysis the proenzyme prothrombin is converted into thrombin. This proteolysis is set in motion by extravascular or intravascular activation processes. The hemostatic equilibrium is regulated not only by activators but also by inhibitors of both coagulation and fibfinolysis. The most important physiological inhibitor of coagulation is antithrombin III (AT III). It inactivates thrombin only to a minor extent initially and in larger measure only after a certain onset time. AT III thus participates directly in an interception mechanism directed against excessive activation of thrombin. A series of pathophysiological conditions leads to consumption of AT III and thus to an increased risk of thrombosis. The clinical picture of disseminated intravascular coagulation, occasionally still designated as consumption coagulopathy, occurs frequently after operations and in conditions of shock. In many cases life-threatening blood clots occur at the same time. Anticoagulants, such as AT III and heparin, and recently hirudin as well, are employed in the therapy of thrombotic disorders, as are coumarin derivatives in prophylaxis. Use of the anticoagulants listed here is associated with disadvantages. Heparin, which is not a single molecule, is only active in the presence of the cofactor AT III. It can only be administered parenterally. Himdin or AT III must be isolated from biological material or prepared by gene technology. Long-term prophylaxis with the coumarins, which are antagonistic to vitamin K, is associated with side effects, such as hemorrhagic skin neeroses, loss of hair and nausea.

For the therapy of thrombotic disorders, low molecular weight anticoagulants have also been developed which act directly on the proteolytically active center of the thrombin, for example serine protease inhibitors, which are derived from a peptide boronic acid. These compounds inhibit not only thrombin but also other serine proteases such as trypsin.

The thrombin inhibitor 2-N-(2-naphthalenesulfonylglycyl)-4-amidino-phenylalanine piperidide (NAPAP) with a thrombin binding constant $K_f=6$ nmol/L is also described, as are derivatives of this structure, in which in particular the aromatic sulfonamide moiety is modified and the amino acid glycine is replaced by other amino acids. The disadvantage of the NAPAP compound, as well the claimed derivatives, lies in the insufficient pharmacological tolerability. In particular, a fall in blood pressure and the release of histamine are observed, while specificity for thrombin and solubility are too low.

It was found, surprisingly, that the N-glycopeptide derivatives 2-N-(4-methoxy- 2,3,6-trimethylbenzenesulfony-N-(β-D-glucuronyl- and β-D-glucopyranosyl)-L-asparaginyl- 4-amidino-D-phenylalanine-piperidide are very effective and specific inhibitors of thrombin (binding constant: $K_f=0.08$ nmol/L) and that their solubility in water is substantially improved.

On the basis of this discovery, the object of the present invention became to prepare novel N-glycopeptide derivatives with anticoagulant activity. This object was achieved by the preparation of the compounds of the formula I.

The invention relates to N-glycopeptide derivatives of the formula I

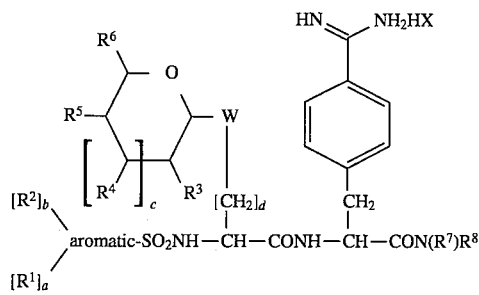

where
aromatic is an unsubstituted or substituted benzene residue, naphthalene residue, chroman residue, chromene residue or coumarone residue, a is 0 to 5, b is 0 to 4, c is 0 or 1, d is 1 or 2

$R^1$ is $(C_1-C_3)$-alkyl, $R^2$ is $(C_1-C_3)$-alkyl or $(C_1-C_3)$-alkyloxy, $R^3$ is H, OH, $(C_1-C_3)$-alkyloxy, $NH_2$, NH-$(C_1-C_6)$-alkanoyl, NH-benzoyl, NH-$SO_3H$ or NH-acyl radical of a natural N-acetylated amino acid, $R^4$ is H, OH, or $(C_1-C_3)$-alkyloxy, $R^5$ is H, OH, $(C_1-C_3)$-alkyloxy, fluorine, chlorine or bromine, $R^6$ is H, $CH_3$, $CH_2OH$, $CH_2O$ —$(C_1-C_6)$-alkanoyl, $CH_2NHCOCH_3$ or $CH_2NH$-$SO_3H$, $R^5$ and $R^6$ are together O—$CH_2$—O—$CH_2$, O-CH($CH_3$)-O-$CH_2$ or

—O—C($CH_3$)$_2$—O—$CH_2$, $R^7$ is hydroxy-$(C_2-C_4)$-alkyl or $(C_2-C_4)$-alkyloxy-$(C_2-C_4)$-alkyl, $R^8$ is H or $(C_1-C_6)$-alkyl or R7-N-R8 are together a pyrrolidine ring, piperdine ring or morpholine ring, which can be substituted by HO, $HOCH_2$, $CH_3$ or COOH, W is —O—, —CONH— or —$C_6H_4$—CONH and H-X is HCl, a $(C_1-C_7)$-alkanoic acid or another pharmacologically tolerated inorganic or organic acid.

Preferred within the framework of the invention are compounds of the formula I,
where
aromatic is an unsubstituted or substituted benzene residue, naphthalene residue or chroman residue, a is 0 to 4, b is 0 to 2, c is 0 or 1, d is 1 or 2 and $R^1$ is $CH_3$, $R^2$ is $CH_3$ or $CH_3O$, $R^3$ is H, OH, $(C_1-C_3)$-alkyloxy, $NH_2$, NH-acetyl, NH-benzoyl, NH-$SO_3H$ or NH-acyl radical of N-acetylglycine or N-acetylalanine, $R^4$ is H or OH, $R^5$ is H or OH, $R^6$ is H, $CH_3$, $CH_2OH$ or $CH_2NH$—$SO_3H$, $R^5$ and $R^6$ are together O—$CH_2$—O—$CH_2$ or O—CH($CH_3$)—O—$CH_2$, $R^7$ is hydroxypropyl or ethoxypropyl, $R^8$ is H or $(C_1-C_6)$-alkyl or $R^7$-N-$R^8$ are together a pyrrolidine ring, piperidine ringor morpholine ring W is —O—, —CONH— or —$C_6H_4$—CONH and H-X is HCl, ($C_1$-$C_6$)-alkanoic acid or another pharmacologically acceptable inorganic or organic acid.

The compounds according to the invention of the formula I may be prepared by reacting a compound of the formula II, where aromatic is an unsubstituted or substituted benzene residue, naphthalene residue, chroman residue, chromene residue or coumarone residue, a is 0 to 5, b is 0 to 4, and $R^1$ is ($C_1$-$C_3$)-alkyl, and $R^2$ is ($C_1$-$C_3$)-alkyl or ($C_1$-$C_3$)-alkyloxy, with an N-glycoside of the formula III,

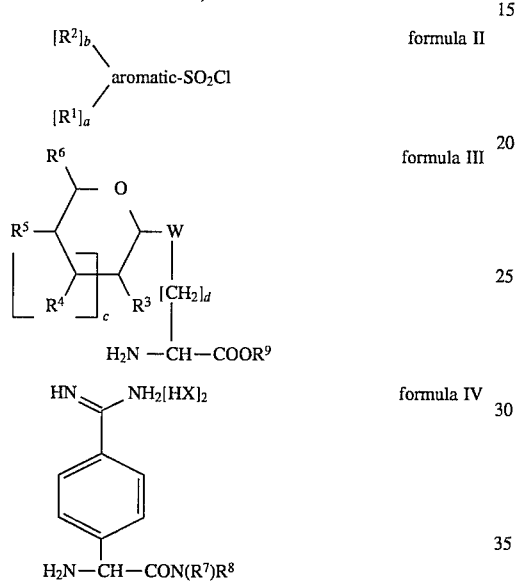

where c is 0 or 1, d is 1 or 2, $R^3$ is H, O protective group, where "protective group" within the framework of this invention is a protective group which is customary in carbohydrate chemistry or peptide chemistry, NH protective group, NH—$SO_3H$, ($C_1$-$C_3$)-alkyloxy, NH-($C_1$-$C_6$)-alkanoyl, NH-benzoyl, NH—$SO_3H$ or NH-acyl radical of a natural N-acetylated amino acid, $R^4$ is H, O protective group or ($C_1$-$C_3$)-alkyloxy, $R^5$ is H, O protective group, ($C_1$-$C_3$)-alkyloxy, fluorine, chlorine or bromine, $R^6$ is H, $CH_3$, $CH_2$-O protective group, $CH_2O$-($C_1$-$C_6$)-alkanoyl, $CH_2NHCOCH_3$, $CH_2NH$—$SO_3H$, $R^5$ and $R^6$ are together O—$CH_2$—O—$CH_2$, O—$CH(CH_3)$—O—$CH_2$ or O—$C(CH_3)_2$—O—$CH_2$ and $R^9$ is a methyl group, tert-butyl group, allyl group or benzyl group and W is —O—, —CONH— or —$C_6H_4$—CONH, and in the presence of an organic base and an organic solvent, to form a sulfonamide compound of the formula V,

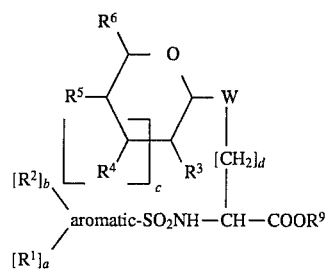

where a, b, c and d and the residues retain their previously indicated meaning, eliminating the radical $R^9$ in the product selectively by hydrolysis with HCl acetic acid or trifluoroacetic acid/water or by hydrogenolysis in the presence of palladium/carbon and a ($C_1$-$C_4$)-alcohol, acetic acid or ethyl acetate as solvent, and reacting the product obtained, in which $R^9$ is a hydrogen atom, with a phenylalanine derivative of the formula IV, where $R^7$ is hydroxy-($C_2$-$C_4$)-alkyl or ($C_2$-$C_4$)-alkyloxy-($C_2$-$C_4$)-alkyl, $R^8$ is H or ($C_1$-$C_6$)-alkyl or $R^7$-N-$R^8$ are together a pyrrolidine ring, piperidine ring or morpholine ring and H-X is HCl, HI or $CF_3COOH$, according to a condensation procedure which is customary in peptide chemistry, to form a compound of the formula I, where a, b, c and d and the residues retain their previously indicated meaning, and removing the protective groups in the product according to procedures which are customary in carbohydrate or peptide chemistry, resulting in the formation of a further product of the formula I, where aromatic is an unsubstituted or substituted benzene residue, naphthalene residue, chroman residue, chromene residue or coumarone residue, a is 0 to 5, b is 0 to 4, c is 0 or 1, d is 1 or 2 and $R^1$ is ($C_1$-$C_3$)-alkyl, $R^2$ is ($C_1$-$C_3$)-alkyl or ($C_1$-$C_3$)-alkyloxy, $R^3$ is H, OH, ($C_1$-$C_3$)-alkyloxy, $NH_2$, NH—($C_1$-$C_6$)-alkanoyl, NH-benzoyl, NH—$SO_3H$ or NH-acyl radical of a natural N-acetylated amino acid, $R^4$ is H, OH, or ($C_1$-$C_3$)-alkyloxy, $R^5$ is H, OH, ($C_1$-$C_3$)-alkyloxy, fluorine, chlorine or bromine, $R^6$ is H, $CH_3$, $CH_2OH$, $CH_2O$—($C_1$-$C_6$)-alkanoyl, $CH_2NHCOCH_3$ or $CH_2NH$—$SO_3H$, $R^5$ and $R^6$ are together O—$CH_2$—O—$CH_2$, O—$CH(CH_3)$O—$CH_2$ or O—$C(CH_3)_2$—O—$CH_2$, $R^7$ is hydroxy -($C_2$-$C_4$)-alkyl or ($C_2$-$C_4$)-alkyloxy-($C_2$-$C_4$)-alkyl, $R^8$ is H or ($C_1$-$C_6$)-alkyl or $R_7$-N-$R_8$ are together a pyrrolidine ring, piperidine ring or morpholine ring, W is —O—, —CONH— or —$C_6H_4$—CONH and H-X is HCl or ($C_1$-$C_6$)-alkanoic acid, and optionally converting the glycopeptide derivative thus obtained into another pharmacologically tolerated salt.

The condensation by the process according to the invention is carried out by the general methods of peptide chemistry, preferably by the method of mixed anhydrides, by way of active esters, azides, or by the carbodiimide method, in particular with the addition of reaction-accelerating and racemization-inhibiting substances such as, for example, 1-hydroxy-benzotriazole (HOBt), N-hydroxysuccinimide, N-hydroxy-5-norbomene-2,3-dicarboximide, additionally using activated derivatives of 1-hydroxybenzotriazole or anhydrides of phosphoric, phosphonic and phosphinic acids at a reaction temperature between −5° C. and 40° C. Suitable solvents for this are dimethylformamide (DMF), dimethylacetamide (DMA), hexamethylphosphoric triamide (HMPT), N-methylpyrrolidone or dimethyl sulfoxide (DMSO). Insofar as the solubility of the components allows, solvents such as methylene chloride, chloroform or dichloroethylene may be employed. The indicated methods are described, for example, in Meienhofer-Gross: "The Peptides", Academic Press, vol. I, (1979).

The choice of the protective groups, which are customary in carbohydrate or peptide chemistry, for amino groups, hydroxyl groups or carboxyl groups is determined by the synthesis strategy as well as the nature of the coupling conditions. Protective groups which are customary in carbohydrate chemistry for the hydroxyl group are understood as meaning, for example, the ($C_1$-$C_{10}$)-acyl protective groups such as ($C_1$-$C_6$)-alkanoyl (e.g. acetyl or monohalogenoacetyl, dihalogenoacetyl or trihalogenoacetyl with halogen being fluorine or chlorine), benzoyl group, methoxybenzoyl group or p-nitrobenzoyl group, as well as optionally modified methyl group, methoxymethyl group, allyl group, benzyl group, tetrahydropyranyl group, benzylidene group, isopropylidene group or trityl group, with the acyl protective groups, in particular the acetyl group, being preferred here.

The amino groups are protected using adamantyloxycarbonyl (Adoc) groups, benzyloxycarbonyl (Z) groups, p-nitrobenzyloxycarbonyl (pNBz) groups, 9-fluorenylmethoxycarbonyl (Fmoc) groups, tert-butyloxycarbonyl (BOC) groups or $\alpha,\alpha$-dimethyl-3,5-dimethoxybenzyloxycarbonyl (DDZ) groups or trifluoroacetyl (TFAc) groups.

The carboxyl groups are protected using ($C_1$-$C_4$)-alkyl groups, allyl (All) groups or benzyl (Bn) groups.

Protective groups can be eliminated by customary methods, in each case according to the nature of the particular group, for example with trifluoroacetic acid, HCl or HBr in acetic acid or by mild reduction, for example with hydrogen and a catalyst, such as palladium/carbon or palladium/barium sulfate in ($C_1$-$C_4$)-alcohol, acetic acid or ethyl acetate. The Fmoc protective group can be eliminated with piperidine, morpholine or other secondary amines, optionally by catalytic hydrogenation (e.g. R. Geiger and W. K önig in E. Gross and Meienhofer (eds.): The Peptides, vol. 3, p. 24, Academic Press 1981).

The O-acyl protective groups and COO-alkyl protective groups are advantageously eliminated in a basic environment, for example with sodium methylate, sodium hydroxide, sodium carbonate, barium oxide or potassium cyanide, or with organic bases, such as, for example, hydrazine in ($C_1$-$C_4$)-alkanol, or their mixtures with chloroform or water.

In the synthesis of the N-glycopeptide building blocks of the formula III, two polyfunctional reactants (carbohydrate and amino dicarboxylic acid) have to be linked. It must be possible to block and deblock both of them selectively. In each case according to the type of N-glycosidic linkage (1,2-cis-N-glycoside or 1,2-trans-N-glycoside) which is being sought, it is necessary to introduce appropriate protective groups for the blocking of the hydroxyl groups, carboxyl groups or amino groups into the glycosyl component as well as the amino acid component, and to work out reaction conditions for the linkage step, which leads stereoselectively to only one of the two possible anomers. For preparing the N-glycopeptide building blocks of the formula III, either the methods known in the literature are used, as described, for example, by A. Y. Khorlin et al. Carbohydr. Res., 85, 201–208 (1980), R. Walczyna and J. Sokolowski, Carbohydr. Res., 180, 147–151 (1988), A. Klemmer and M. Kohla, J. Carbohydr. Chem., 7(4), 785–797 (1988), T. Takeda et al., Carbohydr. Res., 207, 71–79 (1990), W. Guenther and H. Kunz, Angew. Chem., 102/9, 1068 (1990), L. Urge et al., Tetrahedron Letters 32(29), 3445–3448 (1991) and L. Biondi et al., Int. J. Peptide Protein Res., 37, 112–121 (1991), or else modified glycopeptide methods.

With regard to the therapy of thrombotic disorders, the pharmaceutical applicability of the novel compounds of the formula I as anticoagulants was investigated in various in vitro and in vivo test systems. To test the thrombin-inhibiting properties of the novel compounds, inhibition constants ($K_i$) were ascertained with chromogenic substrates in the standardized test. The specificity of the novel compounds towards serine proteases was investigated in particular with thrombin and trypsin. The in vivo activity of the compounds of the formula I was established by determining the acute toxicity ($LD_5$, $LD_{50}$) and partial thromboplastin time (PTT). The chemical stability of the novel compounds with regard to oral administration (passage through stomach and intestine) was ascertained with strong acids and alkalis. The stability of the novel compounds towards degrading enzymes was tested with trypsin and chymotrypsin, as well as indirectly with plasma, and liver or intestinal homogenates.

The invention further relates to pharmaceutical formulations which contain a glycopeptide derivative of the formula I and a pharmaceutical diluent, a solubilizing agent or an excipient.

An advantageous pharmaceutical formulation is the one in which a compound of the formula I is present in the form of an emulsion or a liposomal or micellar preparation. Auxiliaries which can be used for producing a pharmaceutically acceptable formulation are phospholipids, cholesterol, triglycerides, and detergents such as, for example, TweenR 80 or their mixtures. Suitable excipients are, for example, albumins, gelatin polymers such as polygeline or starch, glucose, lactose, mannitol or sorbitol, which are present in a physiological solution or solid form. These formulations contain a therapeutically effective quantity of the glycopeptide compound of the formula I.

In the following examples the present invention is described in more detail, without in this way being limited.

EXAMPLES

The structure of the following compounds was determined by means of $^1$H-NMR spectroscopy, $^{13}$C-NMR spectroscopy and IR spectroscopy, as well as MS analysis and elemental analysis.

Example 1

Preparation of glycosylamines:

Methyl (2,3,4-tri-O-acetyl-β-D-glucopyranosylamine)uronate (Compound 1)

Methyl (2,3,4-tri-O-acetyl-β-D-glucopyranosylazide)-uronate (2.00 g) was dissolved in ethyl acetate/methanol (2:1; 200 mL). After addition of palladium/carbon (2.00 g), the mixture was adjusted with triethylamine to pH 7.5 and then hydrogenareal for one hour. The reaction mixture was filtered and the solution was concentrated in vacuo. Yield: 1.90 g. TLC analysis: Rf=0.35 (dichloromethane/acetone 2:1).

2,3,4,6-Tetra-O-acetyl-β-D-glucopyranosylamine (Compound 2) Starting from 2,3,4,6-tetra-O-acetyl-β-D-glucopyranosyl azide the title compound was prepared as described above.

2-Acetamido-2-deoxy-3,4,6-tri-O-acetyl-β-D-glucopyranosylamine (Compound 3)

Starting from 2-acetamido-2-deoxy-3,4,6-tri-O-acetyl-β-D-hexopyranosyl azide, the title compound was prepared as described above.

Example 2

Preparation of N-glycosides:

2-N-(Fmoc)-4-N-[Methyl (2,3,4-tri-O-acetyl-β-D-glucopyranosyl)uronate]-L-asparagine tert-butyl ester (Compound 4) tert.-Butyl 2-N-(Fmoc)-L-aspartate (1.6 g), HOBt (0.90 g) and dicyclohexylcarbodiimide (1.40 g) were dissolved in THF (100 mL). After stirring for 1 h, the compound 1 (1.4 g) was added to the mixture at 0° C. The mixture was stirred for 16 h at room temperature and subsequently concentrated in vacuo. The residue was diluted with chloroform, extracted by shaking with water, dried with sodium sulfate and evaporated in vacuo. The residue was separated by column chromatography (chloroform/acetone 6:1 ). Yield: 2.00 g; TLC analysis: Rf=0.72 (chloroform/acetone 6:1)

2-N-(Z)-4-N-[Methyl (2,3,4-tri-O-acetyl-β-D-glucopyranosyl)uronate]-L-asparagine tert.-butyl ester (Compound 5) Starting from α-tert.-butyl 2-N-(Z)-L-aspartate (1.5 g) and the compound 1 (1.2 g) the title compound was prepared as described above. Yield: 1.6 g.

2-N-(Z)-4-N-(2,3,4,6-Tetra-O-acetyl-β-D-glucopyranosyl)-L-asparagine tert.butyl ester (Compound 6) α-tert.-Butyl 2-N-(Z)-L-aspartate (3.5 g), HOBt (1.6 g) and DCCI (2.5 g) were dissolved in DMF (160 mL) at 0° C. and then stirred for 1 h. After addition of a solution of compound 2 (3.5 g) in DMF (50 mL), the reaction mixture was stirred for 35 h at room temperature, and then filtered and concentrated by evaporation. The residue was dissolved in dichloromethane and washed with water, and the organic phase was dried over sodium sulfate and concentrated in vacuo. The crude product was purified by column chromatography on silica gel (220 g) with dichloromethane and acetone 5:1. Yield: 3.6 g. [α]D=+2.7° (c=1 in methanol); m.p.=186° C.; TLC analysis: Rf=0.43 (dichloromethane/acetone 3:1).

2-N-(Z)-4-N-(2-Acetamido-2-deoxy-3,4,6-tri-O-acetyl-β-D-glucopyranosyl)-L-asparagine tert.-butyl ester (Compound 7)

2-N-(Z)-L-Asp-O-α-t.-butyl (3.1 g), HOBt (1.4 g) and DCCI (2.3 g) were dissolved in DMF (150 mL) at 0° C. and then stirred for 1 h. After addition of a solution of compound 3 (3.27 g) in DMF (50 mL), the reaction mixture was stirred for 40 h at room temperature, and then filtered and concentrated by evaporation. The residue was dissolved in dichloromethane and washed with water, and the organic phase was dried over sodium sulfate and concentrated in vacuo. The crude product was purified by column chromatography on silica gel (200 g) with dichloromethane and acetone 4:1. Yield: 3.2 g. TLC analysis: Rf=0.55 (dichloromethane/acetone 2:1 ).

2-N-(Z)-4-N-(2-Acetamido-2-deoxy-3,4,6-tri-O-acetyl-β-D-glucopyranosyl)-L-glutamine tert.-butyl ester (Compound 8) Starting from 2-N-(Z)-L-Glu-O-α-t.-butyl (3.0 g) and compound 2 (3.1 g), the title compound was prepared according to the instructions for preparing compound 6.

Example 3

Selective deblocking of N-protective groups of the glycopeptides.

4-N-[Methyl (2,3,4-tri-O-acetyl-β-D-glucopyranosyl)uronate]-L-asparagine tert.-butyl ester (Compound 9)

Method A: The N-Fmoc-protected compound 4 (1.8 g) was dissolved in DMF (40 mL) and piperidine (0.4 mL) was added. After 4 h of stirring, the mixture was concentrated by evaporation in vacuo, and the residue was dissolved in ethyl acetate and butanol 5:1 and washed with dilute hydrochloric acid. The organic phase was dried over sodium sulfate and concentrated in vacuo. The residue was crystallized from ether and petroleum ether. Yield: 0.8 g. M.p.=160°–163° C.

Method B: The N-Z-protected compound 5 (0.9 g) was dissolved in ethyl acetate and methanol 1:1 (20 mL) and hydrogenated in the presence of Pd/C (0.4 g). After filtering off the catalyst, the flitrate was concentrated by evaporation, and the product obtained was used in the next reaction without further purification steps. Yield: 0.75 g.

4-N-(2,3,4,6-Tetra-O-acetyl-β-D-glucopyranosyl)-L-asparagine tert.-butyl ester (Compound 10)

The N-Z-protected compound 6 (2.2 g) was dissolved in ethyl acetate/methanol 1:1 (50 mL) and hydrogenated in the presence of 10% Pd/C (1.3 g) for 4 h. The reaction mixture was filtered off and concentrated by evaporation in vacuo. The product obtained was used for further reaction without any additional purification steps. Yield: 1.63 g. TLC analysis: Rf=0.45 (chloroform/methanol 6:1 )

4-N-(2-Acetamido-2-deoxy-3,4,6-tri-O-acetyl-β-D-glucopyranosyl)-L-asparagine tert.-butyl ester (Compound 11) The N-Z-protected compound 7 (2.2 g) was hydrogenated in the presence of Pd/C and worked up as described above. Yield: 1.63 g. TLC analysis: Rf=0.47 (chloroform/methanol 6:1 )

4-N-(2-Acetamido-2-deoxy-3,4,6-tri-O-acetyl-β-D-glucopyranosyl)-L-glutamine tert.-butyl ester (Compound ! 2)

The N-Z-protected compound 7 (2.2 g) was dissolved in ethyl acetate/methanol 1:1 (50 mL) and hydrogenated in the presence of palladium/carbon (10%: 1.2 g) for 5 h. After filtering off the catalyst, the solution was concentrated in vacuo, and the residue was codistilled twice with toluene. The product obtained (1.32 g) was used without further purification for the following reaction.

Example 4

Preparation of aromatic sulfonyl chlorides:

2,3,4,6-Tetramethyl-benzenesulfonyl chloride (Compound 13) 1,2,3,5-Tetramethyl-benzene (5 mL) was dissolved in dichloromethane (400 mL) and cooled to −10° C. A solution of chlorosulfonic acid (6.6 mL) and dichloromethane (200 mL) was added dropwise, and the mixture was stirred for 3 h and subsequently washed with a 5% solution of sodium hydrogen carbonate and with water, dried over sodium sulfate and concentrated by evaporation. The compound obtained was used for the next reaction without any further purification steps.Yield: 7.64 g. TLC analysis: Rf=0.71 (petroleum ether/ethyl acetate 7:1 ).

Example 5

Preparation of sulfonamides:

2-N-(4-Methoxy-2,3,6-trimethyl-benzenesulfonyl)-4-N-[methyl ( 2,3,4-tri-O-acetyl-β-D-glucopyranosyl)uronate]-L-asparagine tert.-butyl ester (Compound 14)

Compound 9 (1.73 g), diisopropylethylamine (1.2 mL) and 4-methoxy- 2,3,6-trimethyl-benzenesulfonyl chloride (0.80 g) were dissolved in DMF (80 mL). The reaction mixture was stirred for 5 h and subsequently concentrated by evaporation. The residue was dissolved in ethyl acetate and washed with water. The organic phase was dried over sodium sulfate and concentrated by evaporation in vacuo. The crude product was purified by column chromatography on silica gel with dichloromethane and acetone 3:1. Yield: 1.57 g. $[\alpha]_D$=+7.0° (c=1 in methanol); m.p.=108° C.; TLC analysis: Rf=0.87 (dichloromethane/methanol 10:1).

2-N-(4-Methoxy-2,3,6-trimethyl-benzenesulfonyl)-4-N-( 2,3,4,6-tetra-O-acetyl-β-D-glucopyranosyl)-L-asparagine tert.-butyl ester (Compound 15) Compound 10 (1.60 g), diisopropylethylamine (1.0 mL) and 4-methoxy- 2,3,6-trimethyl-benzenesulfonyl chloride (0.78 g) were dissolved in DMF (80 mL). The reaction mixture was stirred for 5 h and subsequently concentrated by evaporation. The residue was dissolved in ethyl acetate and washed with water. The organic phase was dried over sodium sulfate and concentrated by evaporation in vacuo. The crude product was purified by column chromatography on silica gel with dichloromethane and acetone 3:1. Yield: 1.57 g. $[\alpha]D$=+7.3° (c 1.0 in methanol); TLC analysis: Rf=0.37 (dichloromethane and acetone 3:1 ).

2-N-(4-Methoxy-2,3,6-trimethyl-benzenesulfonyl)-4-N-(2-acetamido-2-deoxy- 3,4,6-tri-O-acetyl-β-D-glucopyranosyl)-L-asparagine tert.-butyl ester (Compound 16)
Compound 11 (1.6 g) and 4-methoxy-2,3,6-trimethyl-benzenesulfonyl chloride (0.8 g) were reacted as described above and worked up. Yield: 1.74 g. TLC analysis: Rf=0.36 (dichloromethane/acetone 3:1)

2-N-(4-Methoxy-2,3,6-trimethyl-benzenesulfonyl)-4-N-(2-acetamido-2-deoxy- 3,4,6-tri-O-acetyl-β-D-glucopyranosyl)-L-glutamine tert.-butyl ester (Compound 17)

To a solution of the compound 12 (1.6 g) in DMF (80 mL) were added diisopropylethylamine (1 mL) and 4-methoxy-2,3,6-trimethyl-benzenesulfonyl chloride (0.76 g) while controlling the pH (pH>7.5). The mixture was stirred for 5 h and concentrated by evaporation in vacuo. The residue was dissolved in ethyl acetate and washed with water. The organic phase was dried over sodium sulfate and concentrated. The product obtained was purified on silica gel with dichloromethane and acetone 3:1. Yield: 1.60 g. TLC analysis: Rf=0.82 (dichloromethane/acetone 1:1).

2-N-(2,3,4,6-Tetramethyl-benzenesulfonyl)-4-N-( 2,3,4, 6-tetra-O-acetyl-β-D-glucopyranosyl)-L-asparagine tert.-butyl ester (Compound 18)

Starting from compound 11 and 2,3,4,6-tetramethylbenzenesulfonyl chloride (Compound 13), the title compound was prepared according to the instructions for preparing compound 17.

Example 6

Selective aleblocking of the COO-protective groups of the glycopeptides.

2-N-(4-Methoxy-2,3,6-trimethyl-benzenesulfonyl)-4-N-[methyl-( 2,3,4-tri-O-acetyl-β-D-glucopyranosyl)uronate]-L-asparagine (Compound 19)

Compound 14 (2.20 g) was dissolved in dichloromethane and trifluoroacetic acid 1:1 (50 mL) and subsequently stirred for 2.5 h at room temperature. The reaction mixture was concentrated and the residue was codistilled with toluene. The product obtained was used in the next reaction without further purification steps.Yield: 1.4 g. $[\alpha]_D$+38.2° (c 1.0 in methanol); TLC analysis: Rf=0.22 (dichloromethane/methanol 10:1 )

2-N-(4-Methoxy-2,3,6-trimethyl-benzenesulfonyl)-4-N-(2,3,4,6-tetra-O-acetyl-β-D-glucopyranosyl)-L-asparagine (Compound 20)

Compound 15 (1.5 g) was hydrolyzed with trifluoroacetic acid and worked up as described for compound 19.Yield: 1.0 g. TLC analysis: Rf=0.07 (chloroform/methanol/glacial acetic acid 5:1:0.1 )

2-N-(4-Methoxy-2,3,6-trimethyl-benzenesulfonyl)-4-N-(2-acetamido-2-deoxy- 3,4,6-tri-O-acetyl-β-D-glucopyranosyl)-L-glutamine (Compound 21)

Compound 16 (1.57 g) was hydrolyzed with trifluoroacetic acid and worked up as usual. Yield: 1.31 g. TLC analysis: Rf=0.3 dichloromethane/acetone 1:1 ).

2-N-(4-Methoxy-2,3,6-trimethyl-benzenesulfonyl)-4-N-(2-acetamido-2-deoxy- 3,4,6-tri-O-acetyl-β-D-glucopyranosyl)-L-glutamine (Compound 22)

Compound 17 (1.57 g) was dissolved in dichloromethane (60 mL), and trifluoroacetic acid (20 mL) was added. The mixture was stirred for 6 h, concentrated by evaporation in vacuo and codistilled three times with toluene. Yield: 1.3 g. TLC analysis: Rf=0.83 (dichloromethane/methanol/glacial acetic acid 5:1:0.5).

2-N-(2,3,4,6-Tetramethyl-benzenesulfonyl)-4-N-(2-acetamido-2-deoxy- 3,4,6-tri-O-acetyl-β-D-glucopyranosyl)-L-asparagine (Compound 23) Compound 18 (0.9 g) was hydrolyzed with trifluoroacetic acid as described above. Yield: 0.6 g. TLC analysis: Rf=0.78 (dichloromethane/methanol/glacial acetic acid 5:1:0.5).

Example 7

Condensation step:

2-N-(4-Methoxy-2,3,6-trimethyl-benzenesulfonyl)-4-N-[methyl ( 2,3,4-tri-O-acetyl-β-D-glucopyranosyl)uronate]-L-asparaginyl-4-amidino-D-phenylalanine-piperidide hydrochloride (Compound 24)

Compound 19 (1.0 g), HOBt (0.23 g) and DCCI (0.37 g) were dissolved in DMF (50 mL) and after 0.5 h of stirring 4-amidino-D-phenylalanine-piperidide (as the salt of trifluoroacetic acid: 0.4 g) was mixed in. The reaction mixture was stirred for 48 h at room temperature, and then filtered and concentrated by evaporation in vacuo. The residue was dissolved in ethyl acetate and washed with water. The crude product was purified by column chromatography on silica gel with chloroform/methanol 5:1. Yield: 1.2 g. TLC analysis: Rf=0.7 (chloroform/methanol 3:1).

2-N-(4-Methoxy-2,3,6-trimethyl-benzenesulfonyl)-4-N-( 2,3,4,6-tetra-O-acetyl-β-D-glucopyranosyl)-L-asparaginyl-4-amidino-D-phenylalanine-piperidide hydrochloride (Compound 25)

Compound 20 (2.50 g), HOBt (0.65 g) and DCCI (1.15 g) were dissolved in DMF (100 mL) and after 1 h 4-amidino-D-phenylalanine-piperidide hydrochloride (1.50 g) was mixed in. The mixture was stirred for a further 24 h and concentrated by evaporation in vacuo. The residue was dissolved in chloroform and washed with water. The organic phase was concentrated in vacuo. The crude product obtained was purified by column chromatography on silica gel with chloroform and methanol 3:1.

2- N-(4-Methoxy-2,3,6-trimethyl-benzenesulfonyl)-4-N-(2-acetamido-2-deoxy- 3,4,6-tri-O-acetyl-β-D-glucopyranosyl)-L-asparaginyl-4-amidino-D-phenylalanine-piperidide hydrochloride (Compound 26)

Starting from compound 21 (1.2 g) and 4-amidino-D-phenylalanine-piperidide hydrochloride (0.92 g), the title compound was prepared by reaction as described above and worked up. Yield: 1.32 g TLC analysis: Rf=0.47 (dichloromethane/methanol/glacial acetic acid 5:1:0.5)

2-N-(4-Methoxy-2,3,6-trimethyl-benzenesulfonyl)-4-N-(2-acetamido-2-deoxy- 3,4,6-tri-O-acetyl-β-D-glucopyranosyl)-L-glutaminyl-4-amidino-D-phenyl-alanine-piperidide hydrochloride (Compound 27)

Compound 22 and 4-amidino-D-phenylalanine-piperidide hydrochloride were reacted to give the title compound as described above.

2-N-(2,3,4,6-Tetramethyl-benzenesulfonyl)-4-(2-acetamido-2-deoxy- 3,4,6-tri-O-acetyl-β-D-glucopyranosyl)-L-asparaginyl-4-amidino-D-phenylalanine-piperidide hydrochloride (Compound 28)

Compound 20 and 4-amidino-D-phenylalanine-piperidide hydrochloride were reacted to give the title compound as described above.

Example 8

Deblocking of the O— and COO— protective groups of the glycopeptide derivatives:

2-N-(4-Methoxy-2,3,6-trimethyl-benzenesulfonyl)-4-N-[methyl ([3-D-glucopyranosyl)uronate]-L-asparaginyl-4-amidino-D-phenylalanine-piperidide hydrochloride (Compound 29)

Compound 24 (0.5 g) was dissolved in methanol (50 mL), and the solution was adjusted to pH 9 with 1N NaOH. After 2 h of stirring at pH 8.5–9, the reaction mixture was neutralized with methanolic HCl and concentrated by evaporation in vacuo. The residue was purified by column chromatography (Sephadex LH 20). Yield: 0.44 g. TLC analysis: 0.34 (chloroform/methanol/water).

2- N-(4-Methoxy-2,3,6-trimethyl-benzenesulfonyl)-4-N-[(β-D-glucopyranosyl)-uronic acid]-L-asparaginyl-4-amidino-D-phenylalanine-piperidide hydrochloride (Compound 30)

Barium oxide (0.2 g) was added to a solution of the compound 24 (0.9 g) in chloroform, methanol and water 2:1:0.05 (100 mL). The mixture was stirred for 3 h, and then adjusted to pH 3.5 with methanolic HCl, and concentrated by evaporation in vacuo. The product obtained was purified by column chromatography (Sephadex LH 20). Yield: 0.72 g. TLC analysis: Rf=0.32 (chloroform/methanol/water 8:6:1 ). $[\alpha]_D$=+3.8° (c 0.5 in methanol)

2-N-(4-Methoxy-2,3,6-trimethyl-benzenesulfonyl)-4-N-[(β-D-glucopyranosyl)-L-asparaginyl- 4-amidino-D-phenylalanine-piperidide hydrochloride (Compound 31 ) Barium oxide (0.25 g) was added to a solution of the compound 25 (1.2 g) in chloroform/methanol 2:1 (100 mL) and the mixture was stirred for 2 h and then filtered. The flitrate was neutralized with methanolic HCl and concentrated by evaporation in vacuo. The residue was purified by column chromatography (Sephadex LH 20). Yield: 1.0 g. TLC analysis: Rf=0.04 (chloroform/methanol 3:1)

2-N-(4-Methoxy-2,3,6-trimethyl-benzenesulfonyl)-4-N-(2-acetamido- 2-deoxy-β-D-glucopyranosyl)-L-asparaginyl-4-amidino-D-phenylalanine-piperidide hydrochloride (Compound 32)

Compound 26 (1.0 g) was deacetylated as described above with barium oxide (210 mg) in chloroform and methanol (90 mL). Yield: 0.65 g. $[\alpha]_D$=+15.6° (c 1.013 in methanol)

2-N-(4-Methoxy-2,3,6-trimethyl-benzenesulfonyl)-4-N-(2-acetamido- 2-deoxy-β-D-glucopyranosyl)-L-glutaminyl-4-amidino-D-phenylalanine-piperidide hydrochloride (Compound 33)

Compound 27 was deacetylated with barium oxide as described above.

2-N-(2,3,4,6-Tetramethyl-benzenesulfonyl)-4-(2-acetamido- 2-deoxy-β-D-glucopyranosyl)-L-asparaginyl-(4-amidino-D-phenylalanine-piperidide hydrochloride (Compound 34)

Compound 28 was deacetylated with barium oxide as described above.

Example 9

Synthesis of
p-amidino-D-phenylalanine-morpholinide
N-(tert.-Butyloxycarbonyl)-D-(p-cyano)phenylalanine-morpholinide (Compound 35)

N-(tert.-Butyloxycarbonyl)-D-(p-cyano)phenylalanine (5.0 g) was dissolved in DMF (50 mL). HOBt (2.6 g) and DCCI (4.2) were then added at 0° C. and the mixture stirred for 1 h. Morpholine (1.5 mL) was then added to the mixture, which was stirred for a further 3 h at room temperature, filtered and concentrated by evaporation in vacuo. The residue was dissolved in ethyl acetate and washed in each case three times with a 5% solution of $NaHCO_3$ and a 5% solution of $KHSO_4$. The organic phase was further washed with saturated sodium chloride solution, and then dried over sodium sulfate and concentrated in vacuo. Yield: 6.5 g. TLC analysis: Rf=0.83 (dichloromethane/methanol/glacial acetic acid 10:1:0.5)

N-(tert.-Butyloxycarbonyl)-D-(p-thiocarbamoyl)phenylalanine-morpholinide (Compound 36)

$H_2S$ gas was introduced for 3 hours into a solution of compound 35 (6.5 g) in pyridine (120 mL) and triethylamine (3.2 mL). The reaction mixture was stirred for a further 2 days in a sealed flask, and toluene was then added and the mixture concentrated by evaporation in vacuo. The residue was dissolved in ethyl acetate and washed with a 5% solution of $KHSO_4$. The organic phase was dried over sodium sulfate and concentrated in vacuo. The crude product was crystallized from ethyl acetate and diethyl ether. Yield: 6.7 g. $[\alpha]_D$=−11.3° (c 0.743 in chloroform).

N-(tert.-Butyloxycarbonyl)-D-(p-methylthioimidino)phenylalanine-morpholinide hydroiodide (Compound 37)

A solution of compound 36 (6.5 g) and methyl iodide (5.2 mL) in acetone (150 mL) was maintained under reflux for 0.5 h. The precipitate that was obtained following filtration of the reaction mixture was dissolved in ethyl acetate and washed with ice-water. The organic phase was dried over sodium sulfate and concentrated by evaporation in vacuo. Yield: 7.2 g. $[\alpha]_D$−13.5° (c 1.36 in dichloromethane); TLC analysis: Rf=0.53 (dichloromethane/methanol/glacial acetic acid 10:1:0.5).

N-(tert.-Butyloxycarbonyl)-D-(p-amidino)phenylalanine-morpholinide hydroiodide (Compound 38)

Compound 37 (5.2 g) was dissolved in methanol (80 mL) and ammonium acetate (1.0 g) was mixed in. The mixture was stirred at 60° C. for 3 h and concentrated by evaporation. The residue was purified by column chromatography on LH 20. Yield: 4.2 g. $[\alpha]_D$+7.9° (c 1.45 in methanol)

N-(tert.-Butyloxycarbonyl)-D-(p-amidino)phenylalanine-morpholinide trifluoroacetic acid salt (Compound 39)

Compound 38 (4.0 g) was dissolved in methanol and water 10:1 and sodium trifluoroacetate (5.0 g) was mixed in. The mixture was stirred for 24 h, filtered and concentrated by evaporation in vacuo. The residue was filtered through Sephadex LH 20 support. Yield: 3.2 g.

D-(p-Amidino)phenylalanine-morpholinide trifluoroacetic acid salt (Compound 40)

Compound 39 (3.2 g) was hydrolyzed with trifluoroacetic acid according to customary methods and worked up. Yield: 2.2 g.

Example 10

2-N-(4-Methoxy-2,3,6-trimethyl-benzenesulfonyl)-4-N-(β-D-galactopyranosyl)-L-asparaginyl-4-amidino-D-phenylalanine-piperidide hydrochloride (Compound 41)

2-N-(4-Methoxy-2,3,6-trimethyl-benzenesulfonyl)-L-asparaginyl-4-amidino-D-phenylalanine-piperidide hydrochloride (1.0 g), HOBt (0.23 g) and DCCI (0.37 g) were dissolved in DMF and dichloromethane 1:1 (50 mL) and, after 0.5 h of stirring, β-D-galactopyranosyl-amine (1.0 g) was added. The reaction mixture was stirred for 48 h at room temperature and then filtered and concentrated by evaporation in vacuo. The residue was dissolved in ethyl acetate and washed with water. The crude product was purified by column chromatography on silica gel with chloroform/methanol 5:1. Yield: 1.2 g. TLC analysis: Rf=0.73 (chloroform/methanol 3:1). Barium oxide (0.25 g) was added to a solution of the intermediate compound (1.2 g) in chloroform/methanol 2:1 (100 mL), and the mixture was stirred for 2 h and then filtered. The flitrate was neutralized with methanolic HCl and concentrated by evaporation in vacuo. The residue was purified by column chromatography (Sephadex LH 20). Yield: 1.0 g. TLC analysis: Rf=0.042 (chloroform/methanol 3:1). $[\alpha]_D$+19.3° (c=1 in methanol). M.p. 186°–190° C.

Example 11

Determination of the inhibition constants for thrombin:

The inhibition constants ($K_i$) of the compounds of the formula I were determined in established enzyme-kinetic procedures. The human thrombin which was employed was determined by active site titration to be 87% pure. The test solution for the Ki determination was composed of buffer (50 mM Tris-HCl, 75 mM NaCl, pH 7.8, 37° C.), 100 pM thrombin, 0.1 nM H-D-phenylalanyl-L-pipecolyl-L-argubube-p-butriabukude dihydrochloride (substrate S-2238; from Kabi) and inhibitor, which embraced a range from 0 to 400 nM. Inhibitor and enzyme were preincubated for 10 minutes, and the reaction was started by addition of the chromogenic substrate S2238. For the evaluation of the kinetics, the mathematical algorithm for tight-binding was used, which gave $K_i$ values and the inhibition type with the aid of non-linear regression. The inhibition type was found to be competitive for all the inhibitors.

The results are summarized in Table I.

Example 12

Determination of the specificity of the inhibitors:

The specificity of the inhibitors towards thrombin and trypsin was determined. The $K_i$ of trypsin was determined in an analogous manner to the determination of the $K_i$ of thrombin. The reaction mixture was composed as follows—buffer: 200 mM triethanolamine, 20 mM $CaCl_2$, pH 7.8; 37° C.; enzyme: 0.5 nM trypsin from bovine pancreas; substrate: 500 μM carbobenzoxy-L-valyl-glycyl-L-arginine-4-nitranilide (Chromozyme TRY, from Boehringer Mannheim). The enzymatic reaction was started after a 10 minute preincubation by addition of the substrate. The p-nitroaniline which was liberated was measured at 405 nm. The results are summarized in Table I.

Example 13

Determination of the acute toxicity:

To determine the acute toxicity, CD rats were injected i.v. on day 0 with different doses of the test substance dissolved in 0.5 mL of physiol. NaCl solution. Control groups received only 0.5 mL of physiol. NaCl solution. 2 rats were used per concentration of the test substance. The number of rats surviving on day 1 was determined and the $LD_5$, $LD_{50}$ and $LD_{95}$ were calculated by the Litchfield & Wilcoxon method. The toxicity, $LD_{50}$ (mg/kg), of the compounds described here was determined in comparison with NAPAP. The results are summarized in Table I. Pharmacological data and activities of some selected compounds:

TABLE I

| Compound | Ki thrombin (nmol/L) | Ki trypsin (nmol/L) | Specificity Try/Thr | $LD_{50}$ (mg/kg) (rat) |
|---|---|---|---|---|
| NAPAP | 11 | 499 | 46 | |
| Compound 24 | 0.8 | 231 | 289 | 46 |
| Compound 25 | 2.4 | 283 | 118 | 55 |
| Compound 30 | 0.085 | 349 | 4106 | 51 |
| Compound 31 | 0.075 | 501 | 6680 | 45 |
| Compound 32 | 1.1 | 528 | 480 | 53 |
| Compound 41 | 0.04 | 375 | 9375 | 50 |
| Compound 42 | 1.3 | 650 | 500 | 60 |
| Compound 43 | 1.5 | 187 | 125 | 62 |
| Compound 49 | 0.1 | 531 | 5310 | 52 |
| Compound 50 | 2.1 | 608 | 289 | 64 |

Example 14

Partial thromboplastin time (PTT)-screening test for defects in the intrinsic and extfinsic coagulation system:

The compounds to be tested were administered i.v. as a bolus into the tail vein of the rat. After 5 min blood was removed from a venous plexus and mixed with ⅕ the volume of citrate buffer. PTT was determined in a coagulometer (Schnittger & Gross) with neothrombin. The normal PTT values for the rat are in the region of 20 sec. For the determination of thrombin time (TT), 100 μL of blood, citrate buffer and diethyl barbiturate-acetate buffer were mixed and incubated for 1 min at 37° C. After the addition of 100 μL of test thrombin, TT was determined in a coagulometer.

Example 15

Synthesis of 2-N-(4-Methoxy-2,3,6-trimethyl-benzenesulfonyl)- 3-O-(β-D-ribo-pyranosyl)-L-seryl-4-amidino-D-phenylalanine-piperidide hydroiodide (Compound 42)

Stage 1: Synthesis of 2-N-(4-Methoxy-2,3,6-trimethyl-benzenesulfonyl)-3-O-( 2,3,4-tri-O-acetyl-β-D-ribopyranosyl)-L-seryl-4-cyano-D-phenylalanyl-piperdine: 3-0-(2,3,4-tri-O-acetyl-β-D-fibopyranosyl)-L-serin-tert.-butyl ester (17.3 g), tri-ethylamine (12 mL) and Mlr chloride were dissolved in DMF (800 mL) and stirred at room temperature overnight. The solvent was evaporated off in vacuo, and the residue was raked up in ethyl acetate and washed three times with water. The organic phase was dried with sodium sulfate and evaporated in vacuo. Futher purification was carried out by chromatography on silica gel with dichloromethane/acetone (3:I/V:V). Yield: 15.7 g. Purity check: TLC Rf=0.87 (dichloromethane:methanol/10:1). The intermediate was dissolved in 300 mL of trifluoroacetic acid/dichloromethane (1:1) and stirred at room temperature for 1 h. The acidic mixture was distilled off in vacuo and adherent traces of acid were evaporated off using toluene in vacuo. The resulting product was used without further purification for the next reaction. 10 g from the preceding stage, 2.3 g of HOBt and 3.7 g of DCCI were dissolved in 500 mL of DMF and stirred at 4° C. for 30 minutes. then 9.0 g 4-cyano-D-phenylalanyl-piperdine and 5.0 mL of N-methyl-morpholine were added. The mixture was stirred at room temperature for 18 h and filtered off in vacuo. The crude product was chromatographed on silica gel with chloroform/methanol 5:1 and ethyl acetate. Yield: 14.3 g. TLC Rf=0.86 (chloroform/methanol 10:1 ).

Stage 2: Synthesis of 2-N-(4-Methoxy-2,3,6-trimethyl-benzenesulfonyl)-3-O-( 2,3,4-tri-O-acetyl-13-D-ribopyranosyl)-L-seryl-4-amidino-D-phenylalanylpiperidine×HI:

Cyanophenylalanine glycopeptide (10.0 g) was dissolved in dry pyridine (100 mL) and, after addition of triethylamine (2.5 mL), gaseous hydrogen sulfide was passed for 3 h. The mixture was left to stand at room temperature for 3 days and then poured into a mixture of ice (300 g) and concentated HCl. The precipitate was was filtered off with suction and washed with water. The thioamide was dried and then taken up in acetone (200 mL), and methyl iodide (5.0 mL) was added. The mixture was boiled under reflux for 30 minutes. After cooling, precipitation was induced with diethyl ether. The precipitate was was dissolved in dichloromethane and washed twice with water. The organic phase was dried over sodium sulfate and the solvent was removed, and then the residue (8.2 g) was taken in dry methanol (200 mL), and ammonium acetate (2.1 g) was added. The mixture was heated at 60° C. for 3 h. The solvent was evaporated off in vacuo. The crude was subjected to purification by chromatography on Sephadex LH-20 in methanol and on silica gel with chloroform/methanol/water 10:1:0.2. Yield: 6.2 g. TLC analysis: Rf=0.3 (chloroform/methanol/water 10:1:0.2).

Stage 3: Deacylation of 2-N-(4-Methoxy-2,3,6-trimethyl-benzenesulfonyl)-3-O-( 2,3,4-tri-O-acetyl-β-D-ribopyranosyl)-L-seryl-4-amidino-D-phenylalanylpiperidine×HI:

Barium oxide (0.4 g) was added to a solution of the acetylated compound (1.8 g) in chloroform, methanol and water 2:1:0.05 (200 mL). The mixture was stirred for 3 h, and then adjusted to pH 3.5 with methanolic HCl, and concentrated by evaporation in vacuo. The product obtained was purified by column chromatography (Sephadex LH 20). Yield: 1.42 g (compound 42). TLC analysis: Rf=0.22 (chloroform/methanol/water 8:1:0.2).

Example 16

Synthesis of 2-N-(4-Methoxy-2,3,6-trimethyl-benzenesulfonyl)-L-Asp- 4-amidino-D-phenylalanine-piperidide× HCl (Compound 43)

Compound 43 was prepared as described in German Offenlegungsschrifft DE 4115468 A1

Example 17

Preparation of 2-N-(urethane protecting group)-Asp-α-esters from 2-N-(urethane protecting group)-Asp-β-methyl esters 2-N-BOC-L-asparagine-ct-benzyl ester (Compound 44) N-BOC-L-Asp-β-O-methyl ester (5.0 g) was dissolved in benzyl alkohol (40 mL). KOtert.-butylate was added to a solution, which was heated for 8 h at 60° C. After cooling, the solution was washed twice with water. The organic phase was dried over sodium sulfate and the solvent was removed in vacuo. The residue was crystallized using diethyl ether/petrol ether. Yield: 4.5 g.

2-N-benzyloxycarbonyl-L-asparagine-ct-benzyl ester (Compound 4.5) Starting from N-Z-L-Asp-β-O-methyl ester (5.0 g), the title compound was prepared by reaction as described above and worked up.

2-N-benzyloxycarbonyl-L-asparagine-ct-n-butyl ester (Compound 46) N-Z-L-Asp-β-O-methyl ester (5.0 g) was dissolved in n-butyl alkohol (40 mL). KOtert.-butylate was added to a solution, which was heated for 8 h at 60° C. After cooling, the solution was washed twice with water. The organic phase was dried over sodium sulfate and the solvent was removed in vacuo. The residue was crystallized using diethyl ether/petrol ether. Yield: 4.5 g.

Example 18

Preparation of 2-N-(urethane protecting group)-4-N-glycosyl-asparagine-α-esters, 2-N-(urethane protecting group)-5-N-glycosyl-glutamine-α-esters and 2-N-(urethane protecting group)-4-N-glycosyl-4-amido-phenylalanine esters 2-N-BOC-4-N-β-L-fucopyranosyl-L-asparagine-α-benzyl ester (Compound 47) Starting from compound 44 and β-L-fucopyranosyl-amine, the title compound was prepared by reaction as described in example 2.

2-N-Fmoc-4-N-(2-acetamido-2-deoxy-β-D-glucopyranosyl)- 4-acetamido-L-phenylalanine-α-benzyl ester (Compound 48) Starting from 2-N-Fmoc-4-carboxy-L-phenylalanine-cc-benzyl ester and 2-acetamido-2-deoxy-β-D-glucopyranosyl-amine, the title compound was prepared by reaction as described in example 2.

Example 19

2-N-(4-Methoxy-2,3,6-trimethyl-benzenesulfonyl)-4-N-(β-L-fucopyranosyl)-L-aspaginyl- 4-amidino-D-phenylalanine-piperidide hydrochloride (Compound 49) Compound 47 was deprotected with trifluoroacetic acid/dichloromethane as described in example 6 for compound 19 and the intermediate was reacted with Mtr-chloride as described in example 5. The obtained compound (Mtr- 4-N-glycosyl-Asn-OH) was reacted with 4-amidino-D-phenylalanine-piperidide hydrochloride to give the title compound 49 as described above (Example 7) and worked up.

Example 20

2-N-(4-Methoxy-2,3,6-trimethyl-benzenesulfonyl)-4-N-(2-acetamido- 2-deoxy-β-D-galactopyranosyl)-L-asparaginyl-4-amidino-D-phenylalanine-piperidide hydrochloride (Compound 50)

Stage 1: Synthesis of 2-N-(4-methoxy-2,3,6-trimethyl-benzenesulfonyl)-L-Asn-α-O-benzyl ester 2-N-(4-methoxy-2,3,6-tri methyl-benzenesulfonyl)-L-Asn-β-O-methyl ester (5.0 g) was dissolved in benzyl alkohole (40 mL). KOtert.-butylate was added to a solution, which was heated for 8 h at 60° C. After cooling, the solution was washed twice with water. The organic phase was dried over sodium sulfate and the solvent was removed in vacuo. The residue was cristallized using diethyl ether/petrol ether. Yield: 4.5 g. $[\alpha]_D=+43.3°$ (c=1 in MeOH).

Stage 2: N-Glycosylation:

4.5 g from the preseding stage and 2-acetamido-2-deoxy-β-D-galactopyranosylamine were reacted to give 2-N-(4-Methoxy-2,3,6-trimethyl-benzenesulfonyl)- 4-N-(2-acetamido-2-deoxy-β-D-galactopyranosyl)-L-asparagine-α-O-benzyl ester as described in the example 7. Yield: 4.6 g.

Stage 3: Hydrogenation:

4.6 g from the preseding stage was hydrogenated with Pd/C (2 g) in ethyl-acetate/methanol 1:1 to give Mtr-(2-acetamido-2-deoxy-β-D-galactopyranosyl)-L-asparagine. Yield: 3.55 g.

Stage 4: Condensation step:

Starting from Mtr-(2-acetamido-2-deoxy-β-D-galactopyranosyl)-L-asparagine (3.55 g) and 4-amidino-D-phenylalanine-piperidide hydrochloride (3.3 g), the title compound 44 was prepared by reaction as described above (Example7) and worked up. Yield of compound 50:4.4 g. TLC analysis: Rf=0.47 (dichloromethane/methanol/glacial acetic acid 5:1:0.5), $[\alpha]_D=+21.2°$ (c= 1 in MeOH).

Example 21

Preparation of 2-N-(urethane protecting group)-4-carboxy-phenylalanine and their esters N-Fmoc-4-tert.-butyloxycarbonyl-D and L-phenylalanine-α-benzyl ester (Compounds 51 and 52)

N-Benzyloxycarbonyl-4-cyano-D and L-phenylalanine-α-benzyl ester (5.0 g) was reacted with $H_2S$ and then with methyl iodide as described in example 15 (stage 2) to give S-methyl-thioimide intermediate (4.2 g). The intermediate was hydrolyzed with aq. 5% $KHSO_4$/acetone according to customary method and worked up to give Somethyl-thioester, which was hydrolyzed according to Zemplen method to N-Benzyloxycarbonyl-4-carboxy-phenylalanine-α-benzyl ester. After protection of the carboxy group with tert.-butyl protecting group and hydrogenolysis according to customary method, the intermediate was protected with Fmoc chloride to give the title compound 51 or 52.

We claim:

1. A compound of the formula I

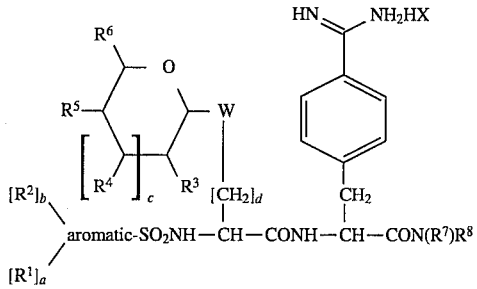

where aromatic is a benzene or naphthalene ring, a is 0 to 3, b is 0 or 1, c is 0 or 1, d is 1, $R^1$ is methyl, $R^2$ is methoxy, $R^3$ is OH, ($C_1$-$C_3$) -alkoxy, $C_1$-acyloxy, $NH_2$ or $C_1$-acylamino, $R^4$ is OH or $C_1$-acyloxy, $R^5$ is OH or $C_1$-acyloxy, $R^6$ is H, $CH_2OH$, $CH_3$, or $CH_2O$-acetyl, N ($R^7$)$R^8$ are together a piperidine ring, W is —O— or —CONH—, and HX is HCl, a ($C_1$-$C_7$) -alkanoic acid or another pharmaceutically tolerated inorganic or organic acid.

2. A compound of the formula I as claimed in claim 1, wherein aromatic is a naphthalene ring.

3. A compound of the formula I as claimed in claim 1, wherein aromatic is a benzene ring, a is 3 and b is 1.

4. A pharmaceutical composition comprising pharmaceutically effective amount of a compound of the formula I as claimed in claim 1.

* * * * *

UNITED STATES PATENT AND TRADEMARK OFFICE
CERTIFICATE OF CORRECTION

PATENT NO. : 5,556,941
DATED : September 17, 1996
INVENTOR(S) : Cenek KOLAR et al.

It is certified that error appears in the above-indentified patent and that said Letters Patent is hereby corrected as shown below:

Title page, item [57], Abstract, line 4, in the formula, "$NH_2HX$", should read --$NH_2$ $HX$--.

Title page, item [57], Abstract, line 18, "$R^6$ is H, $CH_3$, $CH_2OH$, $CH_2O-(C_1-C_6)$," should read --$R^6$ is H, $CH_3$, $CH_2OH$, $CH_2O-(C_1-C_6)$-alkanoyl,--.

Title page, item [57], Abstract, line 26, "piperdine" should read --piperidine--.

Claim 1, column 18, line 10, in the formula, "$NH_2HX$" should read --$NH_2$ $HX$--.

Claim 1, column 18, line 26, "$NH_2$or" should read --$NH_2$ or--.

Claim 4, column 18, line 40, after "comprising", insert --a--.

Signed and Sealed this

Seventeenth Day of June, 1997

Attest:

Attesting Officer

BRUCE LEHMAN

Commissioner of Patents and Trademarks